United States Patent [19]
Dinsmore

[11] Patent Number: 6,111,932
[45] Date of Patent: Aug. 29, 2000

[54] ELECTRON BEAM MULTISTAGE ACCELERATOR

[75] Inventor: Mark Dinsmore, Sudbury, Mass.

[73] Assignee: Photoelectron Corporation, Lexington, Mass.

[21] Appl. No.: 09/211,144

[22] Filed: Dec. 14, 1998

[51] Int. Cl.$^7$ ...................................................... H01J 35/06
[52] U.S. Cl. ................. 378/136; 378/65; 378/15
[58] Field of Search ........................ 378/136, 65; 315/15

[56] References Cited

U.S. PATENT DOCUMENTS

| | | |
|---|---|---|
| 3,949,265 | 4/1976 | Holl . |
| 5,124,658 | 6/1992 | Adler . |
| 5,422,926 | 6/1995 | Smith et al. . |
| 6,009,146 | 12/1999 | Adler et al. . |

*Primary Examiner*—David P. Porta
*Assistant Examiner*—Pamela R. Hobden
*Attorney, Agent, or Firm*—McDermott, Will & Emery

[57] ABSTRACT

A modular multistage accelerator (102) for use in an X-ray treatment system includes a first 10 kV acceleration stage (120) which houses an electron beam gun supplied with −50 kV of voltage. The modular multi-stage accelerator includes four additional 10 kV stages (112,114,116,118) placed in series with the first stage to achieve a 50 kV accelerator overall. Each stage is shielded (190) to prevent stray electrons from being propagated along the length of the drift tube. The triple point within each modular stage is recessed to significantly reduce the emission of stray electrons within each stage. Additionally, the beam current at the X-ray emitting probe of the X-ray source is measured by isolating the beam current to a beam current measuring circuit (220) in electrical connection with a nulling junction node, wherein other currents within the circuit are nulled at the nulling junction node and the beam current flows to the beam current measuring circuit.

16 Claims, 5 Drawing Sheets

ELECTRON BEAM MULTISTAGE ACCELERATOR

BACKGROUND OF THE INVENTION

This invention relates to a miniaturized, programmable X-ray treatment system having an electron beam source and an X-ray emitting probe for use in delivering substantially constant or intermittent levels of X-rays to a specified region and, more particularly, to the electron beam generating components of the X-ray treatment system.

In the field of medicine, radiation is used for diagnostic, therapeutic and palliative treatment of patients. The conventional medical radiation sources used for these treatments include large fixed position machines as well as small, transportable radiation generating probes. The current state of the art X-ray treatment systems utilize computers to generate complex treatment plans for treating complex geometric volumes.

Typically, these systems apply doses of radiation in order to inhibit the growth of new tissue because it is known that radiation affects dividing cells more than the mature cells found in non-growing tissue. Thus, the regrowth of cancerous tissue in the site of an excised tumor can be treated with radiation to prevent the recurrence of cancer. Alternatively, radiation can be applied to other areas of the body to inhibit tissue growth, for example the growth of new blood vessels inside the eye that can cause macular degeneration.

One type of X-ray treatment system used for such applications is disclosed in U.S. Pat. No. 5,153,900 ("'900 patent") issued to Nomikos et al., owned by the assignee of the present application, which is hereby incorporated by reference. The system disclosed in the '900 patent uses a point source of radiation proximate to or within the volume to be radiated. This type of treatment is referred to as brachytherapy. One advantage of brachytherapy is that the radiation is applied primarily to treat a predefined tissue volume, without significantly affecting the tissue in adjacent volumes.

A brachytherapy X-ray treatment system includes an X-ray source 10 shown in FIG. 1, generally comprised of an electron beam ("e-beam") source 12 and a miniaturized insertable probe assembly 14 capable of producing low power radiation in predefined dose geometries or profiles disposed about a predetermined location. The probe assembly 14 includes a shoulder 16 which provides a rigid surface by which the X-ray source 10 may be secured to another element, such as a stereotactic frame used in the treatment of brain tumors. The probe assembly 14 also includes an X-ray emitting tube 18, or "probe", rigidly secured to shoulder 16. A typical probe of this type is about 10–16 cm in length and has an inner diameter of about 2 mm and an outer diameter of about 3 mm.

Typical brachytherapy radiation treatment involves positioning the insertable probe 18 into the tumor or the site where the tumor or a portion of the tumor was removed to treat the tissue adjacent to the site with a "local boost" of radiation. In order to facilitate controlled treatment of the site, it is desirable to support the tissue portions to be treated at a predefined distance from the radiation source. Alternatively, where the treatment involves the treatment of surface tissue or the surface of an organ, it is desirable to control the shape of the surface as well as the shape of the radiation field applied to the surface.

A typical e-beam source 12 of the prior art includes a single 50 kV drift tube acceleration stage or accelerator 20, as shown in FIG. 2. The accelerator 20 includes a cylindrical body 22 comprised of a ceramic portion 24 and a metal portion 26. The accelerator 20 houses an electron gun assembly, including pins 30 which generate electrons and gun 32 which direct the electrons along a central axis 42 of the system through metal tube 38, tube opening 36, probe interface 40, and probe 18 (not shown). The metal portion 26 includes an electrically conductive ring shaped end 28, which includes Node X. The voltage at Node X is ideally 0V during operation and the voltage at Node Y is ideally −50 kV (near the electron gun), thereby providing an acceleration field for the e-beam.

In operation, the e-beam is directed to a target at the distal end of probe 18. The e-beam thus establishes a current along the axis 42. A return current path along the metallic probe 18 couples the distal end of the probe back to Node X at ring 28. The current present at Node X is ideally the beam current ($I_B$), which is measured and an indication of the measurement is communicated to a radiation controller (not shown). The radiation controller adjusts the power supplied to the electron gun 32 as a means of adjusting the beam current and, ultimately, achieving the desired output radiation level at the end of probe 18. As a means of testing and stressing the system, a voltage of 75 kV is applied across Nodes X and Y; this is called "over-voltaging" the system.

A consequence of the single stage 50 kV accelerator 20 of a typical X-ray source 10, is that during operation stray electrons leak out from pins 30 and "avalanche" along ceramic wall 24 and metal wall 26, as shown by arrow 44. These stray electrons are typically emitted form the "triple point" 34, i.e., the point where the negative electrode 30, the vacuum within the accelerator, and the insulator 24 meet. Eventually, the stray electrons strike the end of the accelerator 20 at end 28. At very high voltages, e.g., 75 kV test voltage and 50 kV operational voltage, the electrons incident on metal end 28 have sufficient energy to cause X-rays to be emitted, resulting in unshielded X-rays which may be hazardous to those present. Additionally, the risk of high voltage hazards, such as arcing, are undesirably high while using test voltages the magnitude of 75 kV applied across a single stage. A performance related problem also results from the incident stray electrons on metal 28. The stray electrons cause a "leakage current" to be present at Node X along with the beam current. This stray current is combined with the beam current, leading to an erroneous beam current measurement and resulting calibration of the output radiation by the radiation controller. Consequently, the radiation controller erroneously adjusts the power delivered to the electron gun 32, which alters the beam current and changes the characteristics of the radiation from probe 18. The ability for the system to operate safely and perform adequately at relatively high voltages is a reflection of its "high voltage standoff" capability.

It is an object of the present invention to provide an X-ray source with improved high voltage standoff capability.

It is another object of the present invention to provide electron beam accelerator with improved high voltage standoff capability.

It is a further object of the present invention to provide a modular electron beam accelerator which requires lower voltage stress across the accelerator stages, for testing purposes and to reduce the overall size of an equivalent system.

It is a further object of the present invention to provide an X-ray source with improved radiation accuracy, by achieving improved X-ray source calibration based on accurate beam current measurements.

SUMMARY OF THE INVENTION

These and other objects are achieved by the modular multi-stage accelerator of the present invention. The accelerator includes a first stage, which houses the electron gun used to produce an electron beam. The first stage of the accelerator is cylindrical in shape about a central axis which is common to the system, including an X-ray emitting probe of the system. A header is brazed to one end of the cylindrical first stage, forming a vacuum seal. At the opposite end of the first stage cylinder multiple modular accelerator stages may be added. In the preferred embodiment, the first stage, and each modular stage thereafter positioned along the axis, accelerates an electron using a difference in potential of 10 kV across the stage. A second 10 kV modular stage is brazed to the first stage, with the effect of achieving a 20 kV accelerator, overall. Similarly, a third, a fourth and a fifth 10 kV modular stage may be added, in turn, to achieve a 50 kV accelerator, overall. The particular design of the 10 kV stages accomplishes shielding between stages and thereby provides better high voltage stand-off than previous systems. A base section, substantially ring shaped about the central axis, interfaces the final accelerator stage with the X-ray emitting probe used for treatment.

In the preferred form, the second, third, fourth and fifth modular accelerator stages are substantially identical. Each of these modular stages includes an electrode (anode) and dielectric insulator formed to shield subsequent stages from stray electrons and to dissipate current created by stray electrons. The triple point of each stage is recessed within a cavity formed in the dielectric. When electrons are emitted from the triple point, they are collected by the dielectric in the cavity and ultimately an electric field is created which prevents further emission of electrons from the triple point. Electrons which escape the cavity move into a region between the dielectric and a protrusion of the electrode. Then, because of the conical shape of the insulator and the position of the anode, the electrons propagate directly to the anode. Consequently, avalanching and subsequent arc-over are prevented. Also, because of the shielding and insulating characteristics of each stage, the electrons do not tend to propagate into subsequent accelerator stages.

In order to monitor the output radiation of the X-ray system, it is desirable to measure the beam current of the electron beam delivered to the probe, which requires isolation of the beam current within an X-ray source circuit. In a preferred form, each accelerator stage in the circuit is in electrical connection with a portion of a 10-stage voltage multiplier, which supplies voltage to the accelerator stage, wherein two voltage multiplier stages are dedicated to each single accelerator stage. Each of these electrical connections provides a path for leakage current realized at the cathode of the accelerator stage to be fed back into the multiplier. All of the leakage currents are contained within the multiplier excpet for the last stage. The leakage current from the last stage propagates through the multiplier, exits the multiplier, and flows into a "nulling junction". Additionally, a voltage monitor circuit is provided to measure the output voltage of the power supply and is in electrical connection with the nulling junction. The voltage monitor has a high impedance, so it draws a small current from the nulling junction, which it then feeds back into the voltage multiplier. The multiplier in turn feeds the monitor current back into the nulling junction. Finally, a beam current measuring circuit is also in electrical connection with the nulling junction and in connection with the probe. The beam current at the cathode of the electron gun of the first stage flows through the multiplier and into the nulling junction. As a result, entering the nulling junction are the beam, monitor, and leakage currents. These currents leave the nulling junction via different paths, with only the beam current flowing to the beam current measurement circuit.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

Figure 1:
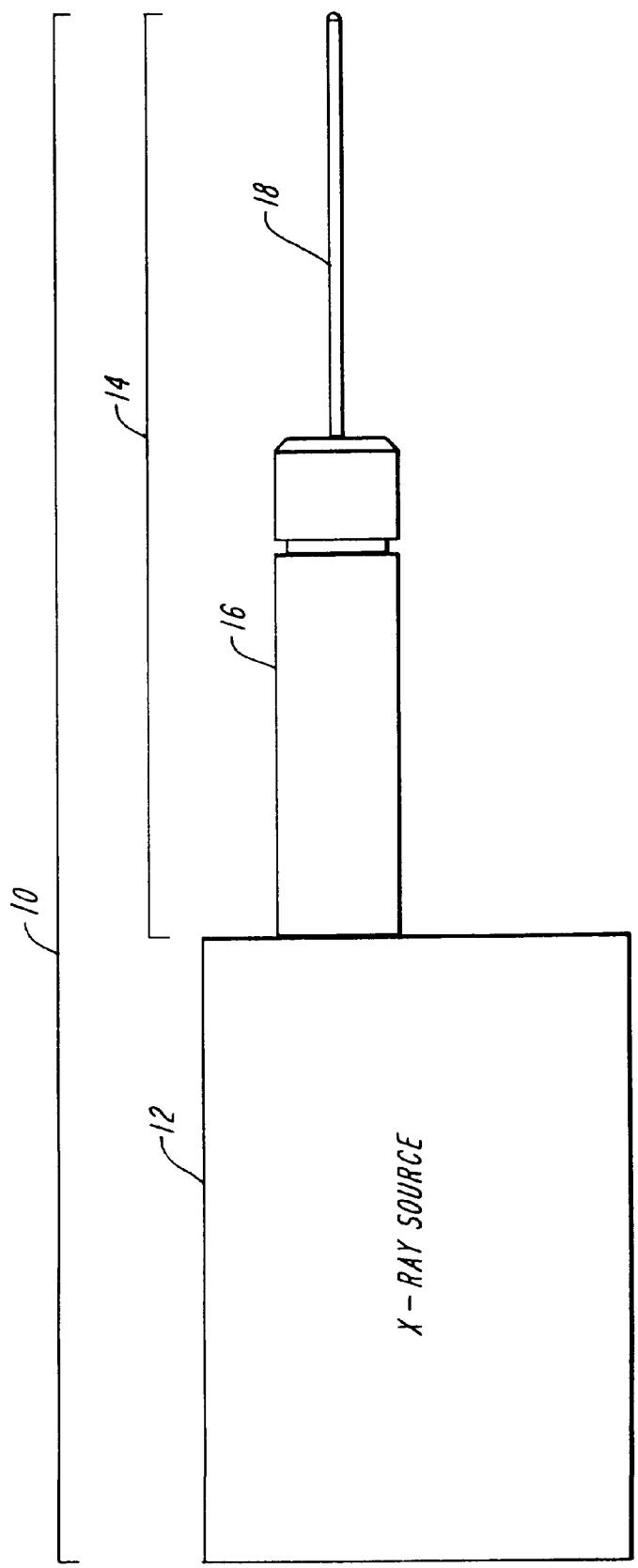
FIG. 1 is a diagrammatic view of an X-ray treatment system X-ray source in accordance with the prior art.
Figure 2:
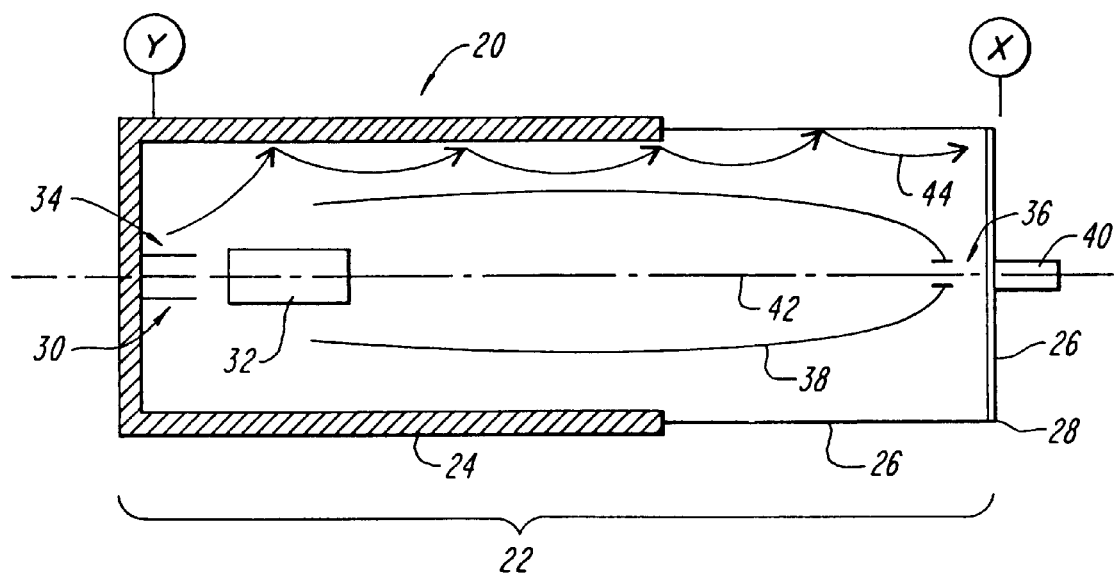
FIG. 2 is a cross-sectional diagrammatic view of the single stage accelerator used in of the prior art system of FIG. 1.

The invention is a multistage modular electron accelerator, which comprises part of an X-ray source of an X-ray treatment system. In the preferred embodiment, the accelerator includes five modular 10 kV accelerator stages placed in serial connection about a central axis, to achieve a 50 kV accelerator. Other sized voltage stages may be used in other embodiments, to establish different overall acceleration.

In the present embodiment, the accelerator achieves high voltage standoff by isolating stray electrons within the stage from which it was emitted and by nulling out any leakage current from the accelerator stages, to allow an accurate measure of the electron beam current. Each 10 kV stage can be tested, i.e., over-voltaged, using 20 kV, which poses relatively low risk of stray X-ray radiation or other high voltage dangers when compared, for example, to over-voltaging a prior art single stage 50 kV accelerator using 75 kV. Because of the shielding characteristics of the modular design, the overall 50 kV modular accelerator may be safely over-voltaged using 75 kV.

Figure 3:
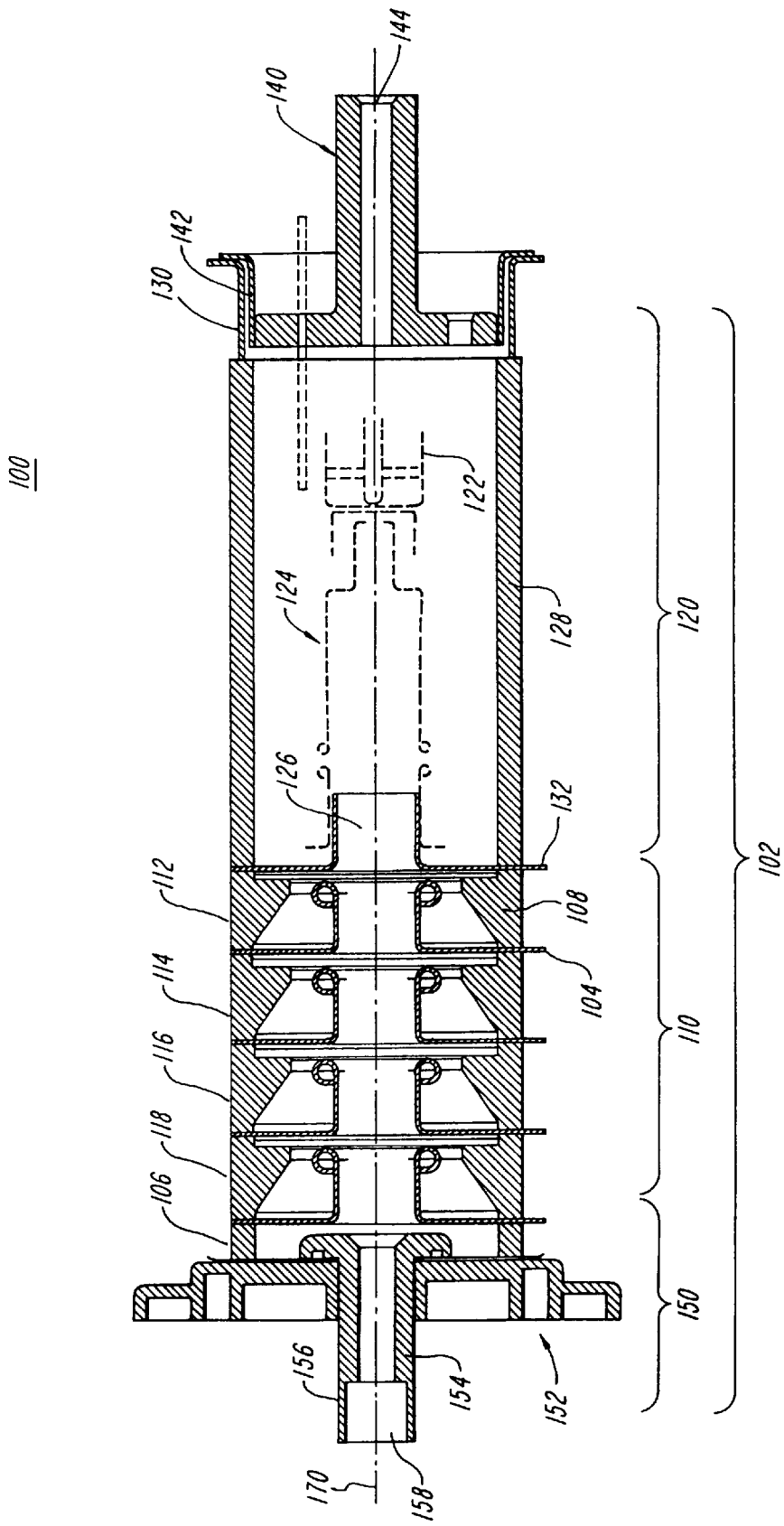
FIG. 3 is a cross-sectional diagrammatic view of the multi-stage accelerator of the present invention.

Referring to FIG. 3, a cross sectional diagram of an X-ray source 100 of an X-ray treatment is shown. The X-ray source 100 includes an accelerator 102 and header 140. Header 140 includes an X-ray window 144. Accelerator 102 includes a first accelerator stage 120 and a plurality of subsequent modular accelerator stages, collectively identified by reference numeral 110, which form a cylindrical accelerator about the common central axis 170. Overall, the accelerator 102 is substantially cylindrical in shape, with one end having an interface to a circular header assembly 140 and an opposite end having a base section 150 which serves as an interface to a cylindrical target tube or "probe" (not shown). It should be appreciated that, while the first stage 120 of the accelerator is required because it houses an electron gun, the additional modular stages 112, 114, 116, and 118 are optional. The decision regarding the number of stages to use may depend on a variety of factors, the most important of which would likely be the desired intensity of the radiation to be supplied by the probe, which is a function of the total acceleration voltage across all stages of the accelerator.

In the preferred embodiment, the first stage 120 of the accelerator 102 includes a ceramic cylindrical body 128, which houses an electron gun 124 and an associated electron gun cathode 122 in an inner region of the body 128. The ceramic body 128 possesses good insulation characteristics, thus reduces the tendency for electrons to stray beyond the inner region of the body 128. One end of the cylindrical body 128 includes a circular body eyelet 130 formed to mate with a similarly sized and shaped circular eyelet 142 of header 140. The body eyelet 130 has an inside diameter which, for example, is 0.090 inches larger than the outside diameter of the header eyelet 142. The header eyelet 142 is nested within and brazed to body eyelet 130, forming a vacuum seal between header 140 and first stage accelerator 120 of accelerator 102. The vacuum seal allows for a controlled environment within the inner region of the accelerator and, therefore, results in a system with strongly predictable performance. In the preferred embodiment, body eyelet 130 and header eyelet 142 are made of Kovar, a material chosen for its thermal expansion qualities, which match those of the ceramic insulator, and because it can be brazed together to form a strong vacuum seal.

At the other end of cylindrical body 128, an interface to the electron gun 124 and to the second accelerator stage 112 is provided. The first stage 120 is terminated at the second accelerator stage 112 with a ring shaped electrode 132 comprised of a high permeability material, such as Mu-metal, which caps the end of cylindrical body 128. The side of the ring shaped electrode 132 external to the inner region of the first stage 120 provides an interface to second accelerator stage 112. The second stage accelerator 112 is cylindrical in shape and has a circumference substantially the same as that of the first stage 120. The two stages are secured together by brazing the circumferential perimeter of the second stage 112 to the circumferential perimeter of the ring shaped electrode 132, to form a vacuum seal. The ring shaped electrode 132 acts as an anode for the first accelerator stage 120 and a cathode for the second accelerator stage 112. A slotted tube 126 protrudes perpendicularly from flat disc electrode 132 and into the inner region of the first stage 120, and about the central axis 170. The slotted tube 126 is formed to be a spring fit with the inside diameter of an emitting end of electron gun 124, sliding in and fixing the axial alignment of that end of the gun relative to the accelerator 102 and central axis 170.

In the preferred embodiment, the electron gun 124 is a commercially available electron gun, Model 2-070 supplied by Clinton Electronics of Loves Park, Ill. The preferred version of electron gun 124 is outfitted with a larger-than-standard cathode and a reversing, double helix heater coil. When the electron gun is operated with a 50 kV accelerating voltage, the heater is at a voltage of 3V and a current of 510 mA and the grid of the electron gun has a <–50V cutoff, with –10 to –18V at 40 micro amps. Also, a first anode (not shown) of the electron gun is substantially at 300V during operation and the second anode is substantially at 10 kV. Under these conditions, a focus voltage of 2900±250V is achieved, which results in a high power and precise diameter electron beam. The gun 124 is designed to operate at voltages of up to 14 kV, so the 10 kV operating voltage required by the first stage 120 is within commercial limits for this model.

The plurality of modular accelerator stages 110 is comprised of four identical modular cylindrical acceleration stages 112, 114, 116, 118 which are coaxial with central axis 170. Each stage includes a ring shaped tapered insulator and a ring shaped electrode, disposed about the central axis 170. In the preferred embodiment, the insulator is made of a ceramic material and the electrode is made of a high permeability alloy, such as Mu-metal. A receiving end of each stage is defined by a circular opening at the end of the cylindrical stage most proximate to the electron gun 124, and has a Mu-metal interface to the previous stage. An emitting end of each stage is defined by an opening at the end of the cylindrical stage most distal to the electron gun, wherein the ring shaped electrode serves as an interface to a subsequent stage. The ring shaped electrode of each stage includes a cylindrical Mu-metal section coaxial with the central axis 170, which protrudes perpendicularly from the flat surface of the ring shaped electrode, parallel to the central axis 170, and toward the electron gun 124. As an example of how the stages are assembled together, the second stage 112 includes a ring shaped tapered alumina insulator 108 which is brazed to ring shaped electrode 132 of the first stage 120. The electrode 104 of second stage 112 is brazed to the insulator of the third stage 114. The stages are brazed together in turn and maintain a vacuum seal within the accelerator 102. The alternating ceramic/metal/ceramic interfaces between stages form strong balanced seals. A balanced seal is one in where thermal stresses on each side of the brazed joint are balanced, which, in this case, has the benefit of greatly reducing the residual shear stress in the joint. Together, the cylindrical protrusions define a tube about a central axis 170, along which the electron beam is projected by the electron gun 124.

Each modular accelerator stage adds 10 kV potential to the sum of the previous stages. That is, the electron gun cathode 122, within the first stage 120, is supplied with –50 kV from an X-ray source power source. A voltage of 10 kV is delivered to electrode 132, placing the anode of the first stage 120 at –40 kV. The difference in the potential of 10 kV between cathode 122 and anode 132 causes an electron (negatively charged) emitted form the electron gun 124 to accelerate toward the electrode (relatively highly positively charged). Because the stages are brazed together to form balanced seals, the interface between the first stage 120 and second stage 112 are at substantially at the same potential of –40 kV. That is, the anode 132 of the first acceleration stage 120 is at the same potential as the cathode of the second accelerator stage 112. The second stage 112 increases the potential by 10 kV, so that the anode of the second stage 104 is effectively at –30 kV, which causes the emitted electron to continue to accelerate from the first stage 120 and through the second stage 112, along the central axis 170. Therefore, when the four stages 112, 114, 116, 118 are added to the first stage 120, a total positive voltage of 50 kV is achieved across the entire accelerator 102. Consequently, the anode of the fifth and final stage is at 0 V.

The base assembly 150 of the X-ray source serves as an interface between the final accelerator stage 118 and a target tube (not shown) of the X-ray treatment system. The base assembly 150 includes a generally circular base member 152 and a mu-metal tube 154, each being coaxial with the central axis 170. The mu-metal tube 154 is brazed to base member 152. Once secured within the base member 152, the mu-metal tube 154 extends through base member 152 and perpendicularly away from the final accelerator stage 118, about central axis 170. The base member 152 is made of an a ceramic sealing alloy, such as Kovar, which can be brazed to a ceramic spacer 106, forming a vacuum seal between the base section 150 and stage 118. The end of the mu-metal tube 154 distal to the last accelerator stage forms a flange 156 which defines a target tube opening 158. A target tube or probe is secured within target tube opening 158 and brazed to flange 156, forming a magnetically shielded brazed seal.

The electrode of the final stage 118 is separated from a disk shaped base member 152 by a short ceramic spacer 106.

The ceramic spacer 106 is ring shaped, having a diameter from the central axis 170 approximately equal to the diameter of the fifth and final accelerator stage 118. The electron beam current ($I_B$) is measured from base member 152 by a beam current measurement circuit and ultimately fed back to a radiation controller within the X-ray treatment system. Measurement of the beam current allows the output radiation at the X-ray emitting probe to be monitored. Since the anode of the final accelerator stage 118 is isolated from base member 152 by ceramic spacer 106, accuracy in the measurement of the beam current at base member 152 is improved.

Figure 4:
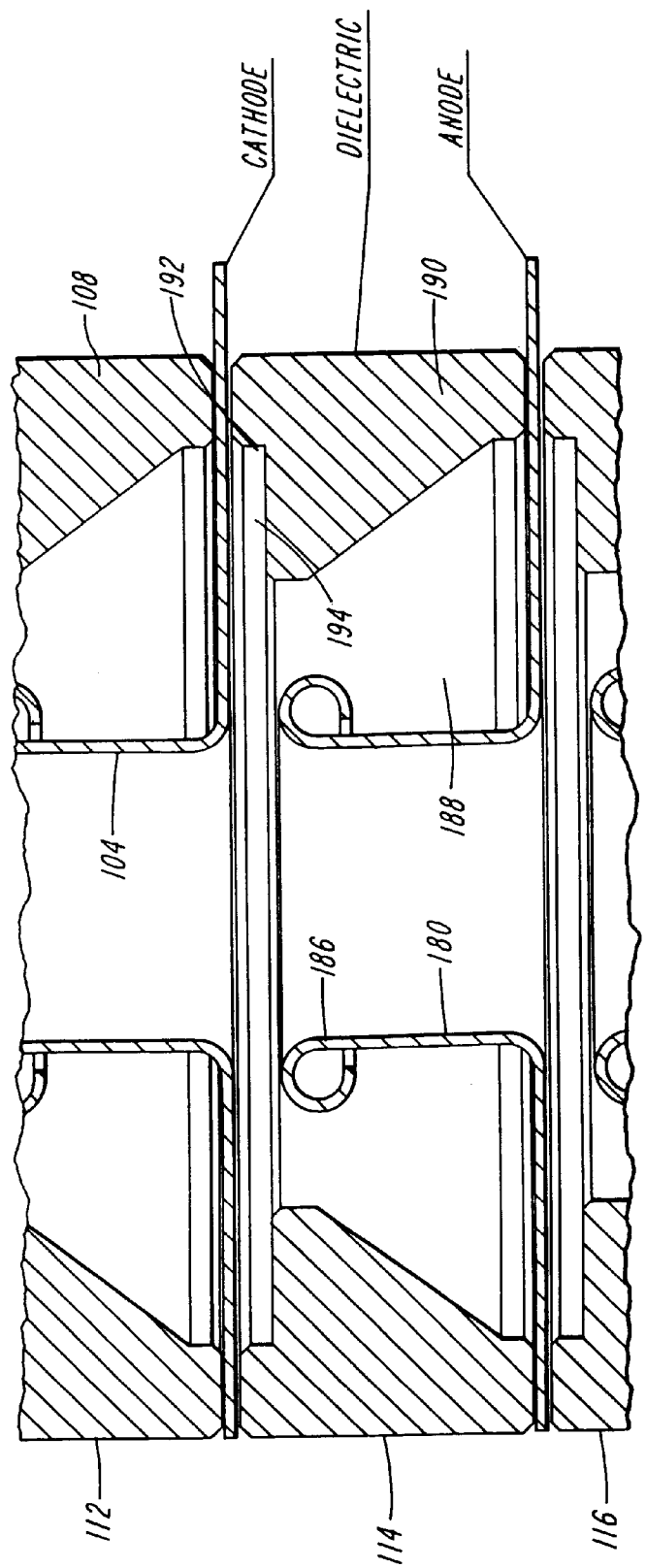
FIG. 4 is a cross-sectional diagrammatic view of the modular accelerator stages of FIG. 3.

Referring to FIG. 4, a partial cross sectional diagram of the modular accelerator stages of FIG. 3 is shown. This particular configuration of electrode 180 and insulator 190 provides increased shielding between each modular accelerator stage and, thereby, reduces high voltage breakdown within the particular accelerator stage and within the accelerator overall. As a result, improved high voltage standoff of the accelerator 102 is realized. The shape of the dielectric 190 is of particular importance in this regard. For example, the triple point 192, i.e., the point where the anode 104 of stage 112, the vacuum and dielectric insulator 190 of stage 114 meet, is recessed within cavity 194. Since the dielectric insulator 190 is at a positive potential relative to anode 104, electrons at the triple point 192 are inevitably attracted to the higher potential dielectric 190. However, the flat surface of the dielectric 190 which forms, in part, cavity 194 accumulates the stray electrons. Therefore, because the dielectric 190 is not a straight wall, the electrons do not avalanche and easily propagate to the next electrode 180. Rather, when enough electrons accumulate on the flat surface of the dielectric 190 a space charge in the cavity 194 reduces the electric field within the cavity 194, at and near triple point 192. Eventually, the difference in potential between the cavity 194 and the electrode 104 is eliminated and electrons cease being emitted from triple point 192. Thus, the leakage from the triple point 192 is greatly reduced.

The inverted conical shape of the dielectric 190 eliminates possible secondary emission and breakdown effects caused by electrons that happen to escape cavity 194 or get emitted from electrode 104. In either case, stray electrons are caught and trapped within a void region 188, between the dielectric 190 and electrode 180. The electrode (anode) 180 serves as a physical barrier between accelerator stages. As a result, stray electrons are attracted to electrode 180. The loop 186 formed at the top of the protrusion of the electrode 180, along with the radius of the electrode, serve to reduce voltage stresses in the gap between cathode 104 and anode 180. The insulation material, i.e., dielectric, of the next stage prevents electrons from leaking from electrode 180 into the next layer. And, the current caused by the stray electrons within the electrode 180 flows into the X-ray source circuitry and are nulled therein, as will be discussed herein. As a result, effective shielding between modular acceleration stages is achieved.

The multistage accelerator also provides additional benefits. Voltage breakdown across an insulator in a vacuum has been shown to be roughly proportional to the square root of the insulator height. Therefore, multiple stages of smaller height shielded insulators results in a shorter assembly for the same voltage standoff capability. Also, diminishing the voltage per stage, from 50 kV for one stage to 10 kV for each of five stages, allows the diameter of each stage to be decreased, reducing the overall volume of the acceleration cylinder. This permits fabrication of a smaller X-ray source, reducing mass and volume of the system.

The voltage stress per stage required for testing the 50 kV modulator accelerator is relatively small. Because each stage is a 10 kV stage, as opposed to a single 50 kV stage accelerator, each stage can be tested (i.e., over-voltaged) with a 20 kV voltage, rather than using 75 kV to over-voltage a 50 kV single stage accelerator. The use of 20 kV over-voltage instead of 75 kV over-voltage inherently decreases the risk of high voltage dangers. For example, the danger of the X-ray treatment system causing undesired and harmful X-ray emissions during testing from stray electrons is far less likely using an over-voltage of 20 kV than it is using an over-voltage of 75 kV. Also, the risk of arcing is greatly reduced when the test voltage is 20 kV, rather than 75 kV. Additionally, if the entire multistage modulator accelerator is tested using a 75 kV over-voltage, the shielding between accelerator stages ensures that stray electrons will not be accelerated using 75 kV along the entire accelerator, so the risk of harmful extraneous X-ray radiation is substantially eliminated.

Figure 5:
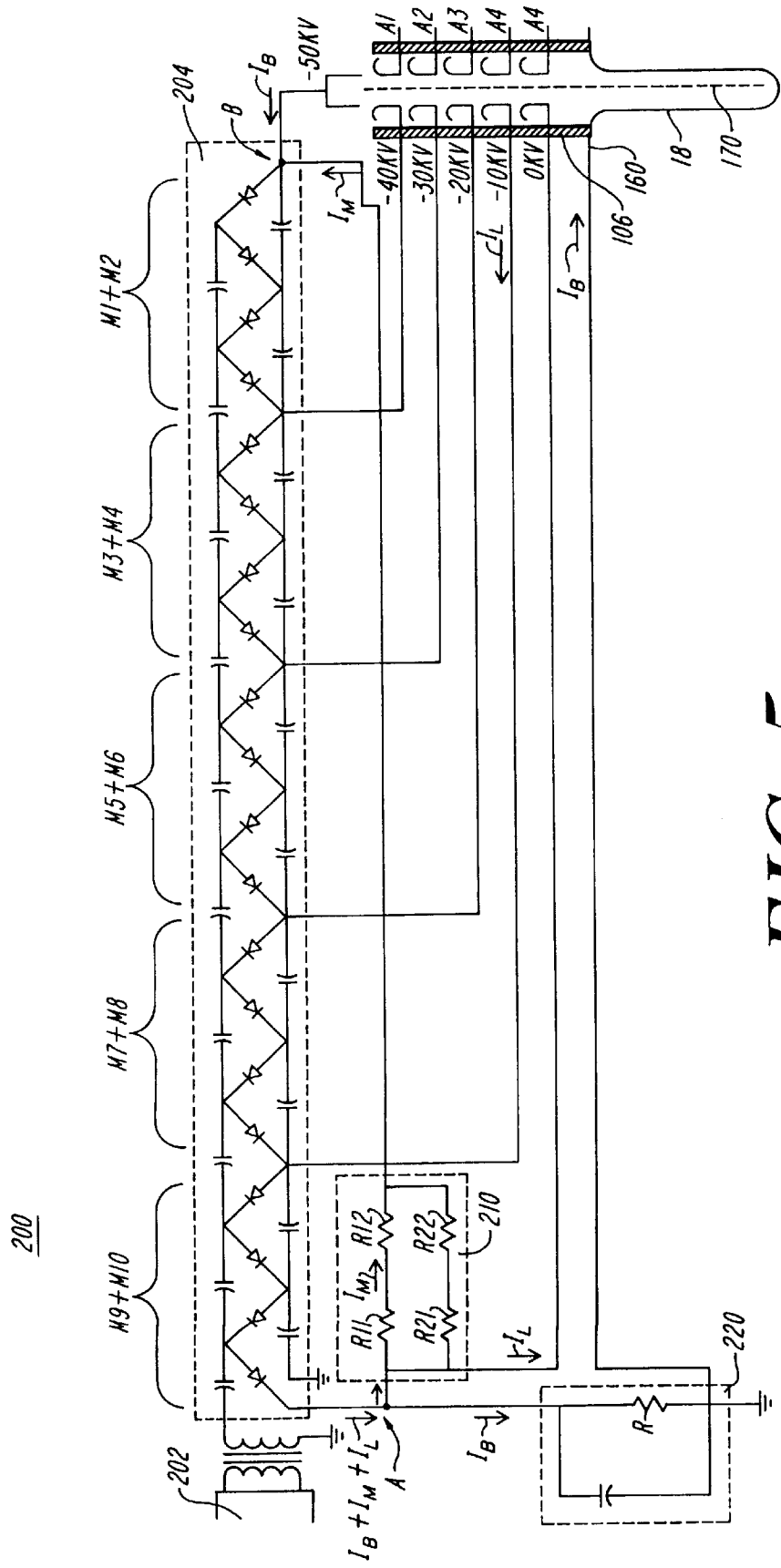
FIG. 5 is a schematic diagram of a portion of the X-ray source circuit which isolates the beam current to a beam current measurement circuit, in accordance with the present invention.

FIG. 5 shows a circuit diagram 200 of the X-ray source of the present invention. A voltage of −50 kV is supplied to the cathode 122 of the electron gun 124, which is housed within the first stage 120 of the accelerator 102, by a 10-stage voltage multiplier 204 in electrical connection with the electron gun cathode 122 at Node B, wherein the multiplier 204 is fed by a power supply 202. Consequently, a current is passed back from the cathode 122 of electron gun to the 10-stage multiplier 204 via Node B. This is the current used to form the electron beam and is referred to as the beam current ($I_B$). As shown in FIG. 5, a separate 2 stages of the 10-stage multiplier are in electrical connection with and supply voltage to each of the five accelerator stages (A1–A5). That is, multiplier stages M1 and M2 supply a 10 kV potential to the cathode of the first accelerator stage (Al), multiplier stages M3 and M4 supply 10 kV to the cathode of the second accelerator stage (A2), and so on. This continues until the voltage at the anode of the fifth accelerator stage (A5) is 0 Volts, as described by the following accelerator equation:

$$0\ V = -50\ kV + 10\ kV(A1) + 10\ kV(A2) + 10\ kV(A3) + 10\ kV(A4) + 10\ kV(A5).$$

Additionally, each electrical connection between a multiplier stage and its corresponding accelerator stage provides a path for any leakage current realized within a given accelerator stage to be dissipated back into the multiplier. The leakage current from stage A5, referred to as $I_L$, passes from the multiplier into the nulling junction, Node A.

The circuit 200 provides for the measurement of the voltage output by the power supply 202, using voltage monitor circuit 210. In the preferred embodiment, the resistors of the monitor circuit 210 are chosen to be of very high impedance, so that only a small current is drawn by the monitor circuit 210, which reduces errors in measuring the beam current. For example, in preferred form R11 and R21 are each 1 megohms and R12 and R22 are each 10 gigohms. The monitor circuit current $I_M$ is drawn from nulling junction Node A and passes through the monitor circuit 210 and into the 10-stage multiplier at Node B. The monitor circuit current propagates through the 10-stage multiplier and back into Node A. The monitor circuit 210 is shown with identical parallel legs, the first leg containing R11 and R12 in series and the second leg containing R21 and R22 in series. The second leg provides redundancy for the first leg, so in a less robust design the second leg could be omitted.

The X-ray source circuit 200 also includes a beam current measurement circuit 220. As noted earlier with respect to FIG. 3, the beam current may be read at base electrode 160, which is in electrical connection with probe 18. The beam current flows from the beam current measurement circuit 220, and therefore originally from Node A, and into the base electrode 160 and probe 18. As will be appreciated by those skilled in the art, electrons from the base electrode 160 actually flow to the beam current measurement circuit 200, and so it is the current at the probe 18 which the circuit is measuring, rather than the current at the electron gun cathode 122. The current is measured across resistor R, which is a 10 k ohm resistor in the preferred embodiment, within the beam current circuit. The configuration of the of the X-ray circuit 200 acts to isolate the beam current $I_B$ from other currents in the circuit, such as $I_L$ and $I_M$. The current equation at nulling junction Node A demonstrates how the beam current is isolated to the beam current measurement circuit 220, as follows:

$$I_B \text{ (into Circuit 220)} = I_B + I_L + I_M \text{ (from multiplier)} - I_L - I_M.$$

Therefore, the X-ray source circuit provides for accurate measurement of the beam current.

The invention may be embodied in other specific forms without departing from the spirit or central characteristics thereof. The present embodiments are therefore to be considered in all respects as illustrative and not restrictive, the scope of the invention being indicated by appending claims rather than by the foregoing description, and all changes that come within the meaning and range of equivalency of the claims are therefore intended to be embraced therein.

What is claimed is:

1. A modular multistage electron beam accelerator, for use in an electron beam source of an X-ray source, wherein the X-ray source includes the electron beam source for generating and directing an electron beam along a central axis and an X-ray emitting probe extending from the electron beam source along said central axis, the modular multistage accelerator comprising:

A. an elongated accelerator first stage, including:
      i. an insulated first stage housing formed about said central axis and defining a central void region within said first stage housing;
      ii. an enclosed and insulated first end of the elongated first stage housing;
      iii. a second end of said first stage housing, opposite the first end and proximate to the X-ray emitting probe relative to the first end, having an opening defined therein about said central axis and a first stage anode affixed thereto; and
      iv. an electron gun, including an electron gun cathode, disposed within the first stage housing such that electrons emitted from the electron gun are directed along the central axis toward said second end;
   B. an electron gun power source in electrical connection with said electron gun cathode, wherein the electron gun emits electrons in response to a voltage supplied to said electron gun cathode by said electron gun power source; and
   C. a first stage power source in electrical connection with the first stage anode, such that a positive first stage accelerator voltage delivered to the first stage anode causes electrons emitted from the electron gun along said central axis to accelerate toward the second end along said central axis.

2. The modular multistage electron beam accelerator of claim 1, wherein the voltage delivered to the electron gun cathode by the electron gun power source is −50 kV.

3. The modular multistage electron beam accelerator of claim 1, wherein the positive voltage delivered to the first stage anode by the first stage power source is 10 kV relative to the electron gun cathode.

4. The modular multistage electron beam accelerator of claim 1, further comprising:

D. a second accelerator stage, including:
      i. an insulated second stage housing formed about said central axis and defining a central void region within said second stage housing;
      ii. a third end, defined by said second stage housing, vacuum sealed to and in electrical connection with the second end of the first stage and having an opening formed therein about said central axis, wherein the third end and the second end are maintained at the same voltage and the anode of the elongated accelerator first stage serves as the cathode of the second accelerator stage;
      iii. a fourth end, defined by said second stage housing, opposite said third end, having an opening defined therein about said central axis and a second stage anode affixed thereto;
      iv. a second stage power source in electrical connection with the second stage anode, such that a positive second stage accelerator voltage delivered to the second stage anode causes electrons propagated along said central axis from the first accelerator stage to be accelerated toward the fourth end along said central axis.

5. The modular multistage electron beam accelerator of claim 4, wherein the positive voltage delivered to the second stage anode by the second stage power source is 10 kV relative to the second stage cathode.

6. The modular multistage electron beam accelerator of claim 4, wherein the insulated second stage housing is comprised of:
   a ring shaped insulator having a recess formed in the ring shaped insulator at the third end, proximate to the vacuum seal with the second end of the first stage, wherein electrons emitted from a juncture of the second stage anode, central void region of the second accelerator stage, and ring shaped insulator are trapped in said recess.

7. The modular multistage electron beam accelerator of claim 6, wherein an inner surface of the second stage insulator defines the second stage central void region to be substantially conical in shape, about the central axis, wherein the base of the conical second stage central void region is proximate to the second stage anode.

8. The modular multistage electron beam accelerator of claim 6, wherein the insulator is made from a ceramic material.

9. The modular multistage electron beam accelerator of claim 6, wherein the second stage anode is comprised of:
   A. a flat anode ring, defining a ring opening about the central axis; and
   B. an anode cylinder disposed about the central axis, having a diameter substantially the same as the diameter of the ring opening, wherein the cylinder is integral with said anode ring at a first end of said anode cylinder and a second end of said anode cylinder is radially curved away from the central axis.

10. The modular multistage electron beam accelerator of claim 4, further comprising:

E. a third accelerator stage, including:
       i. an insulated third stage housing formed about said central axis and defining a central void region within said third stage housing;

ii. a fifth end, defined by said third stage housing, vacuum sealed to and in electrical connection with the fourth end of the second stage and having an opening formed therein about said central axis, wherein the fifth end and the fourth end are maintained at the same voltage and the anode of the second stage serves as the cathode of the third stage;

iii. a sixth end, defined by said third stage housing, opposite said fifth end, having an opening defined therein about said central axis and a third stage anode affixed thereto;

iv. a third stage power source in electrical connection with the third stage anode, such that a positive third stage accelerator voltage delivered to the third stage anode causes electrons propagated along said central axis from the second accelerator stage to be accelerated toward the sixth end along said central axis.

11. The modular multistage electron beam accelerator of claim 10, wherein the positive voltage delivered to the third stage anode by the third stage power source is 10 kV relative to the third stage cathode.

12. The modular multistage electron beam accelerator of claim 10, further comprising:

F. a fourth accelerator stage, including:
   i. an insulated fourth stage housing formed about said central axis and defining a central void region within said fourth stage housing;
   ii. a seventh end, defined by said fourth stage housing, vacuum sealed to and in electrical connection with the sixth end of the third stage and having an opening formed therein about said central axis, wherein the seventh end and the sixth end are maintained at the same voltage and the anode of the third stage serves as the cathode of the fourth stage;
   iii. an eighth end, defined by said fourth stage housing, opposite said seventh end, having an opening defined therein about said central axis and a fourth stage anode affixed thereto;
   iv. a fourth stage power source in electrical connection with the fourth stage anode, such that a positive fourth stage accelerator voltage delivered to the fourth stage anode causes electrons propagated along said central axis from the third accelerator stage to be accelerated toward the eighth end along said central axis.

13. The modular multistage electron beam accelerator of claim 12, wherein the positive voltage delivered to the fourth stage anode by the fourth stage power source is 10 kV relative to the fourth stage cathode.

14. The modular multistage electron beam accelerator of claim 12, further comprising:

G. a fifth accelerator stage, including:
   i. an insulated fifth stage housing formed about said central axis and defining a central void region within said fifth stage housing;
   ii. a ninth end, defined by said fifth stage housing, vacuum sealed to and in electrical connection with the eighth end of the fourth stage and having an opening formed therein about said central axis, wherein the ninth end and the eighth end are maintained at the same voltage and the anode of the fourth stage serves as the cathode of the fifth stage;
   iii. a tenth end, defined by said fifth stage housing, opposite said ninth end, having an opening defined therein about said central axis and a fifth stage anode affixed thereto;
   iv. a fifth stage power source in electrical connection with the fifth stage anode, such that a positive fifth stage accelerator voltage delivered to the fifth stage anode causes electrons propagated along said central axis from the fourth accelerator stage to be accelerated toward the tenth end along said central axis.

15. The modular multistage electron beam accelerator of claim 14, wherein the positive voltage delivered to the fifth stage anode by the fifth stage power source is 10 kV relative to the fifth stage cathode.

16. The modular multistage electron beam accelerator of claim 14, further comprising:

H. a ring shaped insulated probe interface, including:
   i. a probe interface housing formed about said central axis and defining a central void region within said probe interface housing;
   ii. an eleventh end, defined by said probe interface housing, vacuum sealed to the tenth end of the fifth stage and having an opening formed therein about said central axis; and
   iii. a twelfth end, defined by said probe interface housing, opposite said eleventh end, having an opening defined therein about said central axis and a beam current measurement electrode affixed thereto, wherein said X-ray emitting probe is affixed to said twelfth end of said probe interface.

* * * * *